(12) United States Patent
Krause

(10) Patent No.: US 7,963,928 B2
(45) Date of Patent: Jun. 21, 2011

(54) AUTOMATED BIOPSY AND DELIVERY DEVICE

(76) Inventor: William R. Krause, Charlottesville, VA (US)

( * ) Notice: Subject to any disclaimer, the term of this patent is extended or adjusted under 35 U.S.C. 154(b) by 0 days.

(21) Appl. No.: 11/638,114

(22) Filed: Dec. 13, 2006

(65) Prior Publication Data

US 2007/0123797 A1 May 31, 2007

Related U.S. Application Data

(63) Continuation-in-part of application No. 10/858,112, filed on Jun. 1, 2004, now Pat. No. 7,169,114.

(60) Provisional application No. 60/749,587, filed on Dec. 13, 2005.

(51) Int. Cl.
*A61B 10/00* (2006.01)
(52) U.S. Cl. .......................................... 600/562; 600/568
(58) Field of Classification Search ................. 600/564, 600/565, 562, 566, 567, 568; 606/172; 128/754
See application file for complete search history.

(56) References Cited

U.S. PATENT DOCUMENTS

| | | | | |
|---|---|---|---|---|
| 5,146,921 A | * | 9/1992 | Terwilliger et al. | 600/567 |
| 5,980,545 A | * | 11/1999 | Pacala et al. | 606/170 |
| 6,022,324 A | * | 2/2000 | Skinner | 600/566 |
| 6,436,054 B1 | * | 8/2002 | Viola et al. | 600/562 |
| 2006/0074342 A1 | * | 4/2006 | Hibner | 600/566 |

FOREIGN PATENT DOCUMENTS

WO  WO 02/051300 A2 * 11/2001

* cited by examiner

*Primary Examiner* — Max Hindenburg
*Assistant Examiner* — Renee Danega
(74) *Attorney, Agent, or Firm* — Sheldon H. Parker, Esq

(57) ABSTRACT

An automated device for obtaining a tissue biopsy and delivering material to provide hemostatis, therapeutic agents or marker material is described. The device has an outer casing, a power source, a drive mechanism, an application chamber through which the biopsy mechanism, typically a cutting needle, passes through and an application channel. The cutting biopsy mechanism has a mechanical or electromechanical mechanism to rapidly fire a stylet with a biopsy trough into the intended tissue and then rapidly propel a biopsy cannula over the stylet to sever and retain tissue that has protruded into the biopsy trough. At least one application channel is formed by a tube centrically slipped over the biopsy cannula wall. To enable the collection of tissue specimens, the distal segment of the application channel forms a close fitting and concentric sheath around the biopsy cannula.

16 Claims, 17 Drawing Sheets

AUTOMATED BIOPSY AND DELIVERY DEVICE

CROSS-REFERENCE TO RELATED APPLICATIONS

This application makes reference to the following co-pending U.S. Patent Applications. The first application is U.S. App. No. 60/749,587, entitled "Automated Biopsy and Delivery" filed Dec. 13, 2005 and claims the benefit thereof. The second application is U.S. application Ser. No. 10/858,112, entitled "Biopsy and Delivery Device," filed Jun. 1, 2004, now U.S. Pat. No. 7,169,114 from which this is a continuation-in-part. The entire disclosure and contents of the above applications are hereby incorporated by reference.

BACKGROUND

1. Field of the Invention

The present invention relates to a device that automatically takes a biopsy or other sample of human or animal tissue and delivers a coagulant or other material to the biopsy incision track in order to plug the track and prevent bleeding, to provide a marker for future reference so that it may be located in a subsequent medical/surgical procedure or place a material or chemical to prevent seeding of cells from the biopsy site.

2. Related Art

In modern medical practice small tissue samples, known as biopsy specimens, are often removed from tumors, lesions, organs, muscles and other tissues of the body for histological evaluation and diagnosis. Such removal of tissue samples can be accomplished by open surgical technique (i.e., removal of a small sample of tissue through a small surgical incision using a local anesthetic), or through the use of a specialized biopsy instrument such as a biopsy needle. After the tissue samples have been removed, they are typically subjected to diagnostic tests or examinations such as a) gross and microscopic examination to determine cytology and/or histology, b) biochemical analyses to determine the presence or absence of chemical substances which indicate certain disease states, c) microbiological culturing to determine the presence of bacteria or other microbes, and/or d) other diagnostic procedures. The information obtained from these diagnostic tests and/or examinations can then be used to make or confirm diagnoses and/or to formulate treatment plans for the patient. Special Considerations Relating to Biopsy and Plugging the Biopsy Track to Prevent Bleeding; Liver Biopsy Excision biopsy of the liver has traditionally been the gold standard for assessing the extent of injury and determining prognosis in chronic viral hepatitis, non alcoholic steptohepatitis, fatty liver disease and liver cancer. A significant complication that frequently occurs is bleeding from the biopsy site. Significant hemorrhage occurs in 0.35 to 0.5% of all procedures while evidence of sub-clinical bleeding, as detectable by ultrasound 24 hours post biopsy, has been reported in up to 23% of patients. A smaller amount of surface bleeding is almost universal and is frequently associated with mild to moderate pain.

Excision biopsies from other organs, such as the lungs, also exhibit a relatively high complication rate due to hemorrhagic incidents and pneumothorax. Also with kidney biopsies and biopsies of other organs, perfuse bleeding is considered the most important complication.

In order to prevent bleeding resulting from the biopsy, it has been proposed to plug the biopsy channel with a hemostatic agent. A typical hemostatic agent can be Gelfoam (Pharnacia & Upjohn), Avitene (Davol, Inc), FloSeal (Baxter International) or other similar agent. The treatment of a biopsy track with an injectable absorbable coagulant to facilitate homeostasis in conjunction with procuring a biopsy provides substantial advantages in comfort over external pressure methods or the insertion of a pledget of Gelfoam foam as described in U.S. Pat. No. 6,086,607, which must be inserted through a previously inserted catheter. The insertion of a catheter involves a longer procedure as well as the risk of the catheter shifting while the operator switches or disconnects from the aspiration biopsy syringe to the coagulant delivery syringe. In addition, the present invention also provides advantages over the insertion of an absorbable sponge material in a dry state with an applicator. A dry piece of sponge material must be cut to the particular size of the biopsy track and does not swell to fill the track until the blood has sufficiently saturated the sponge material which can take a significantly amount of time and provides inadequate local compression.

From Austrian Pat. No. 384,165, a biopsy needle device of the initially defined kind is known, with which the cannula has a curved partition wall towards the internal limitation of the cannula lumina. Therein, the partition wall does not reach immediately to the front end of the cannula so that the biopsy channel and the application channel communicate in the region of the tip of the cannula. The multi-lumen biopsy device according to Austrian Pat. No. 384,165 enables the collection of tissue and the application of substances plugging the puncture track in coordination with the puncturing procedure in one operating cycle, thus largely shortening the time of intervention.

U.S. Pat. No. 4,850,373 and related EP patents 243341 A, B1 etc., also describes a biopsy needle device having a two lumen cannula, a biopsy channel of constant cross section and one application channel. The application channel is formed by a tube eccentrically slipped over the biopsy channel wall. Furthermore, the biopsy channel is described as a non-circular tubular structure with its channel wall flattened in cross section such that an application channel is formed between the flattened side of the biopsy channel wall and the outer application tube. In addition, surface contact exists between the non-flattened side of the biopsy channel wall and the application tube.

A common surgical material used to control bleeding is Gelfoam®, which is supplied in either a powder form or as an implantable sponge. Sterile sponges, such as Gelfoam®, are prepared in dry sterile sheets that are used as packing material during surgery for control of bleeding. The sponge sheets are left in the surgical site after surgery to stop bleeding and are absorbed by the body in 1 to 6 weeks. A number of techniques have used these absorbable sterile sponge materials to plug a biopsy track to minimize or prevent bleeding. The absorbable sponge provides a mechanical blockage of the track, encourages clotting, and minimizes bleeding though the biopsy track. Despite the advantages of using absorbable sponge to plug a biopsy track this technique has not achieved widespread use because of difficulty in preparing and delivering the sponge material into the biopsy track.

One example of a biopsy wound closure device using an implantable sponge is described in U.S. Pat. No. 5,388,588. According to this patent, a circular sponge of an absorbable foam material is precut and inserted into a biopsy site by an applicator rod having the sponge positioned on the end. Once the sponge is implanted, the sponge absorbs blood and swells to fill the track preventing further bleeding at the biopsy site. However, the sponge is difficult to deliver and expands slowly once delivered. In addition, this delivery method can only deliver a sponge of a limited size that provides less local compression than desired and may incompletely fill the target site. Further, bleeding may continue along sections of the biopsy track where no sponge has been delivered.

Another example of a Gelfoam® inserting device to facilitate hemostasis is described in U.S. Pat. No. 6,086,607. According to this patent, a method of cutting a piece of Gelfoam® sponge from a sheet of the material, folding the strip to form a pledget with one end of different cross section than the other end, and inserting the pledget in an adapter to compress the pledget and for attachment to a syringe for delivery of the pledget to the tissue. The adapter is attached to a cannula that was previously inserted into the organ being biopsied and the Gelfoam® is inserted into the tissue through the cannula.

Cutting Needle Technique

As can be seen from Table 1, many cutting biopsy surgical appliances are currently known. Typically, the instrument consists of a long, thin probe, termed a stylet, within a close-fitting hollow needle, termed a cannula. The stylet and cannula are contained within or attached to a firing device that first projects the stylet into the tissue, followed immediately by the cannula. The stylet has a notch into which tissue will prolapse when the stylet enters the tissue. As the cannula slides over the stylet, a small piece of tissue is then severed from the organ mass and captured within the notch of the stylet. The instrument is then withdrawn and the piece of tissue removed from the stylet for evaluation.

TABLE 1

Commercially Available Cutting/core Biopsy Devices

Automated Cutting Devices

| | |
|---|---|
| CR Bard | Bard Max-Core Disposible Biopsy System |
| Cooke Inc | Coaxial Quick-Core Biopsy Sets |
| Boston Scientific | ASAP ™ |
| Semi-Automated Cutting Devices | |
| Allegiance Healthcare Corp | Temno Biopsy System |
| Avid Medical | Spring loaded |
| Ranfax Medical | |
| Remington Medical | Remington Sharp Cut |
| Cone Instruments | TZ Spring loaded |

Griffith, U.S. Pat. No. 3,477,423, was one of the first to describe an economical and simplified, biopsy needle device in which a cannula is projected forward over the stylet with a recessed collection notch such that the tissue within the notch is severed and retained within the cannula for retrieval. Improvements over the years have lead to single handed, semi automatic driving devices as described by U.S. Pat. No. 4,944,308, U.S. Pat. No. 5,368,045 and U.S. Pat. No. 5,951,489.

Special Considerations Relating to Biopsy and Delivering a Marker Material: Breast Biopsy Breast cancer is presently the most common cancer in women and is the second leading cause of cancer deaths in women. Periodic physical and radiographic examination of the breasts (mammography) is important for early detection of potentially cancerous lesions in women over 40 years of age. In mammography, the breast is compressed between two plates while specialized x-ray images are taken. If an abnormal mass in the breast is found by physical examination or mammography, ultrasound may be used to determine whether the mass is a solid tumor or a fluid filled cyst. Cystic lesions are generally benign and the diagnosis of a cystic lesion is often confirmed by needle aspiration of fluid from the interior of the cyst and immediate diagnosis. However, solid masses are usually subjected to some type of tissue biopsy to determine if the mass is cancerous. This determination requires that the tissue be processed which may require 24 to 48 hours.

Therefore in order to locate the site of the biopsy and cancerous tissue for removal or radiographic treatment at a subsequent procedure, the site is marked, either externally or internally, with a biopsy site marker. Various types of biopsy site markers have been known in the prior art. U.S. Pat. No. 2,192,270 (Carswell, Jr.) and U.S. Pat. No. 5,147,307 (Gluck) describes externally applied markers. Additionally, the prior surgical procedures have included radiographically visible markers that may be introduced into the biopsy site such as marker wires that are inserted through the biopsy needle after a tissue sample is removed and are thereafter allowed to remain protruding from the patient's body. U.S. Pat. No. 6,161,034 (Burbank) describes various chemical preparations and methods for marking biopsy sites which remain present and detectable for up to 5 to 8 months from the initial biopsy. A method for simultaneously taking the biopsy sample and delivering the marker material is not described.

In co-pending application U.S. patent application Ser. No. 10/858,112 (Krause) for a "Biopsy and Delivery Device", filed Jun. 1, 2004, the forgoing problems were overcome. This application teaches the combination of the multi lumen, concentric needle device providing an assembly for obtaining the biopsy and an application channel with a syringe for delivering the application material using a mechanized delivery system. The prior art does not describe the combination of a cutting needle biopsy device with a syringe application device for delivery of the application material and a device which automatically takes the biopsy and delivers the application material.

The present invention, as described herein, provides a device which facilitates the means to take the biopsy specimen and deliver a hemostatic agent to minimize the bleeding from the biopsy tract. The invention describes an electro-mechanical device to accomplish the procedure. Other mechanisms such as pneumatic, hydraulic, magnetic and electrical could also be used to perform the same tasks as known by those skilled in the art.

SUMMARY OF THE INVENTION

The present invention provides a fully automated biopsy device with a view to enabling the collection of tissue specimens for biopsy and to apply auxiliary substances directly in the site of the puncture without tissue specimens getting into the application cannula, thus obstructing the same, or having to change instrumentation. Using the invention the clinician, using customary percutaneous biopsy technique, inserts the tip of the biopsy needle into the liver, or subject organ or organ, activates the device that automatically takes a biopsy and then delivers the coagulant or other material into the biopsy track.

The disclosed device uses a syringe tube to which is attached to an application channel formed by a tube of varying or constant cross section slipped over the biopsy mechanism channel wall. The biopsy mechanism is typically a commercially available spring action or core biopsy device. The stylet and cannula of the biopsy mechanism is typically positioned through the plunger of the coagulant syringe with the biopsy needle passing through the inner end of the plunger, the seal, coagulant chamber and the application channel. The application channel can also contain separate channels for fiber optic cables for the transmission of light or laser energy used in the photo initiation of delivered material.

Using commercially available biopsy equipment, a biopsy is achieved according to the invention in that after the tissue specimen is collected in the biopsy channel of the biopsy needle, the inner tube containing the tissue specimen is retracted within the concentric outer application tube thus allowing the application material to be injected into the biopsy track without obstruction. After obtaining a biopsy, the biopsy syringe is retracted within the application syringe plunger that is depressed by which the application material is expelled from the application chamber into the biopsy site. This may be facilitated by a placing the biopsy device in another device according to the invention that causes the translations and movements of the parts of the fore mentioned biopsy device.

BRIEF DESCRIPTION OF THE DRAWINGS

The invention will be described in conjunction with the accompanying drawings, in which.

DETAILED DESCRIPTION

Figure 1:
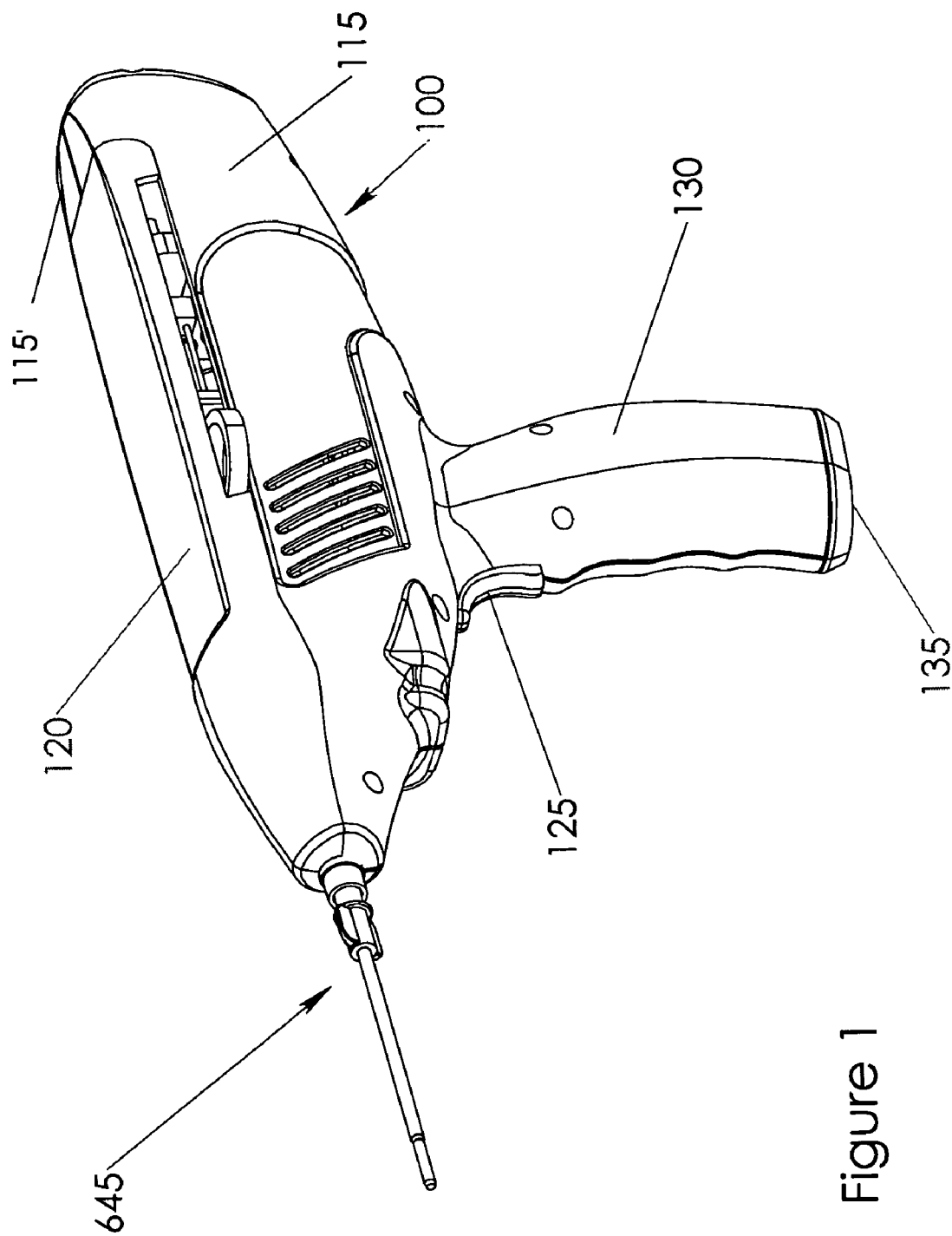
FIG. 1 is a perspective view of the automated biopsy device in accordance with an embodiment of the present invention.

It is advantageous to define several terms before describing the invention. It should be appreciated that the following definitions are used throughout this application.

For the purposes herein the term "biopsy" shall refer to the tissue sample retrieved from the body for evaluation of a possible disease tissue.

For the purposes herein the term "circuit boards" shall refer to any board, or other device that mechanically supports and electrically connects electronic components using any type of conductive pathway.

For the purposes herein the term "coagulant" shall refer to any material ha the process of which causes blood to form solid clots.

For the purposes herein the term "cannula" shall refer to a thin walled tube.

For the purposes herein the term "hemostasis" shall refer to the stopping or arresting of bleeding.

For the purposes herein the term "motor" shall refer to any device having the ability to convert a source of energy into a mechanical motion.

For the purposes herein the term "proximity sensors" shall refer to a electrical or mechanical component that detects an object within a close distance.

For the purposes herein the term "stylet" shall refer to a slender wire with a section removed for the purpose of collecting a specimen of tissue.

For the purposes herein the term "core biopsy" or needle biopsy, shall refer to any biopsy in which tissue is "obtained by insertion through the skin with a specifically designed needle that detaches tissue with an inner needle so that it can be brought to the surface in its lumen." Dorland's Illustrated Medical Dictionary 27$^{th}$ Edison, Copyright W. B. Saunders Company, 1988.

The system of the present invention automatically collects and retrieves a biopsy specimen and then delivers, with or without removal of the biopsy assembly, an application material to facilitate hemostasis of the biopsy track or other puncture wound in a simple and safe manner. The device according to the invention causes the translations and movements of the parts of the disclosed biopsy device to procure a biopsy specimen and deliver the coagulant material to the biopsy track.

The delivered application material can also be used to provide a marker or subsequent procedures such as radiation or surgical treatments. The apparatus for collecting the biopsy specimen and delivering a coagulant materal will be described below in connection with procurement of a liver biopsy sample for the diagnosis of certain liver diseases. However, the automated biopsy device can be used for the procurement of other biopsy specimens from other vascular organs as well as facilitating hemostasis of other types of puncture wounds or tissue access tracks to prevent bleeding of these wounds. The invention can also be used for the procurement of a biopsy specimen and the delivery of a marker, therapeutic or other substance into the biopsy site.

The current means of obtaining a biopsy specimen from the liver is either using the aspiration technique or the cutting needle technique. The aspiration technique utilizes a common syringe and 15 to 18 gauge needle for obtaining the biopsy by the technique described by Menghini and Jamshidi. Briefly, the needle is inserted to the surface of the organ to be biopsied, penetrating slightly, suction is applied to the syringe and the needle is then advanced into the organ while maintaining suction. The needle is withdrawn from the body and the specimen flushed from the needle. In another means, a cutting needle is inserted into the organ, or tissue, and the mechanism activated causing a stylet with a specimen trough to penetrate deeper into the tissue. A cutting sheath moving outward over the stylet then cuts and entraps the tissue that had protruded into the trough. The needle is then withdrawn from the body and the specimen retrieved.

A complication with either technique is that after removal of the biopsy device, the tissue bleeds from the resulting biopsy tract. In the liver, the biopsy site will typically bleed up to 5 minutes however, if a major artery within the liver is hit, the bleeding can be severe requiring immediate operative intervention. The design of the disclosed automated biopsy device provides a number of advantages, including the elimination or reduction of bleeding.

FIG. 1 illustrates the assembled fully automated biopsy device 100 of the invention including an outer casing consisting of a left 115 and right 115' half including a handle 130, a removable top piece 120, a removable battery pack 135 and a trigger mechanism 125 used to control the operation of the device. The exposed portion of the syringe/biopsy assembly 645 is also seen In the FIG. 12. As can be seen from FIG. 1, the biopsy device 100 is easily held and operated with one hand.

Figure 2:
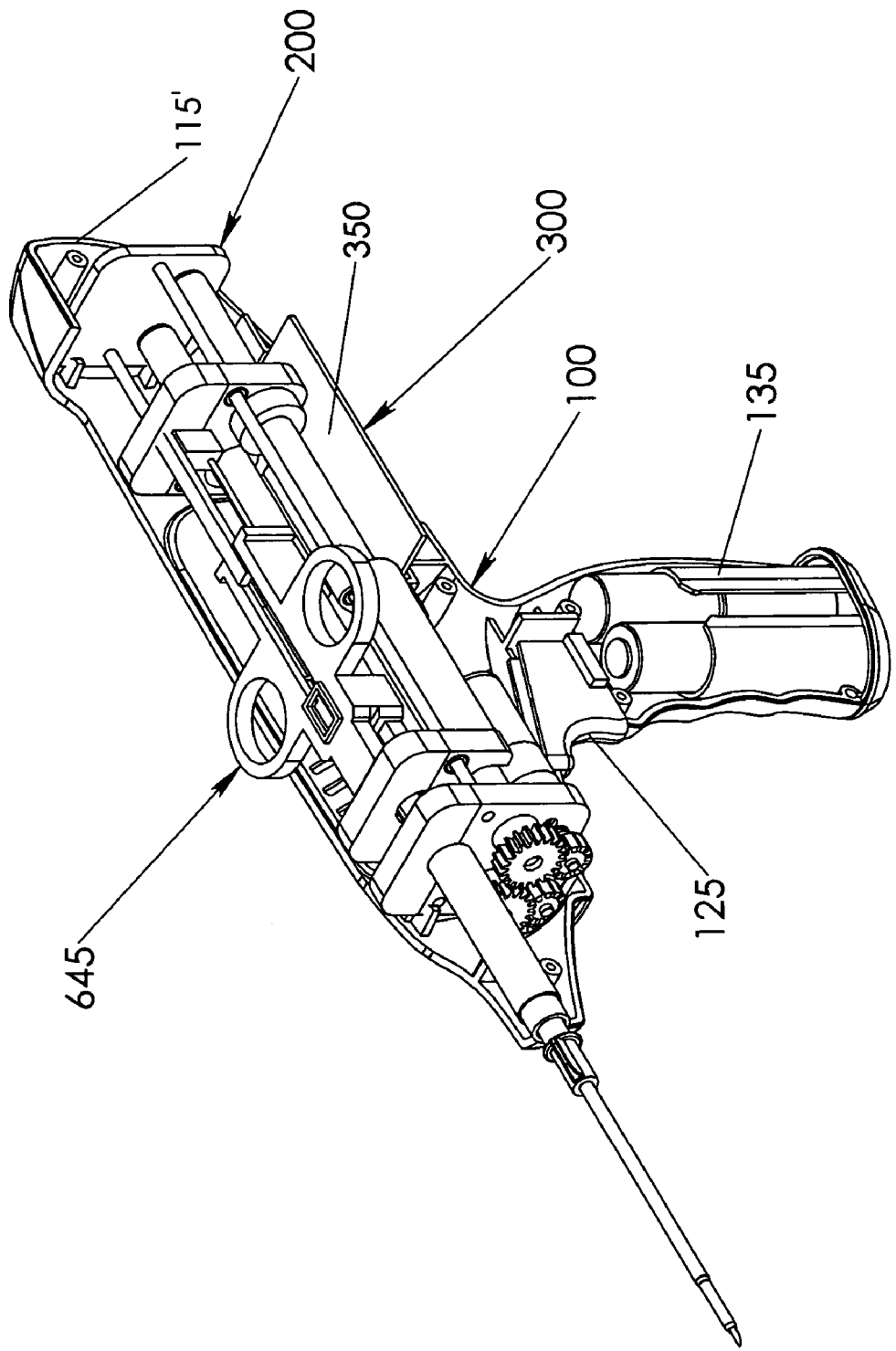
FIG. 2 is a cutaway view of the interior of the biopsy device of FIG. 1 accordance with an embodiment of the present invention.
Figure 4:
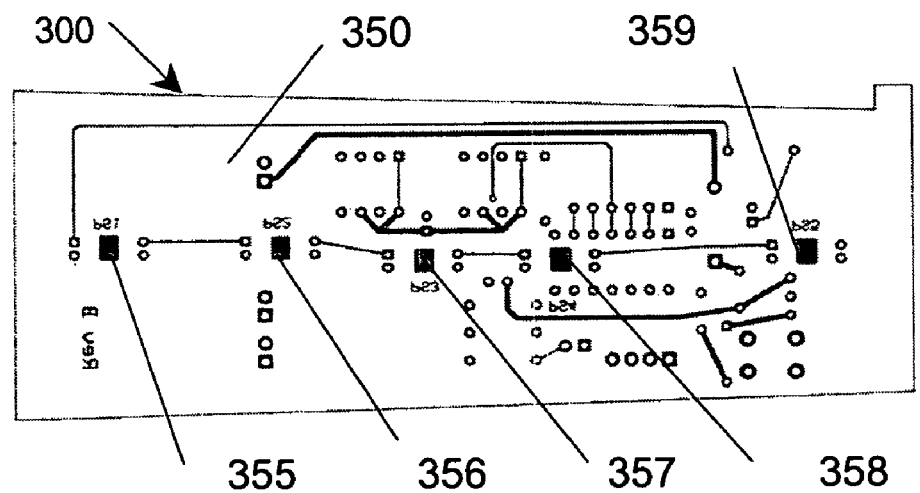
FIG. 4 is a top view of a circuit board for use in the device of FIG. 1 accordance with an embodiment of the present invention.
Figure 5:
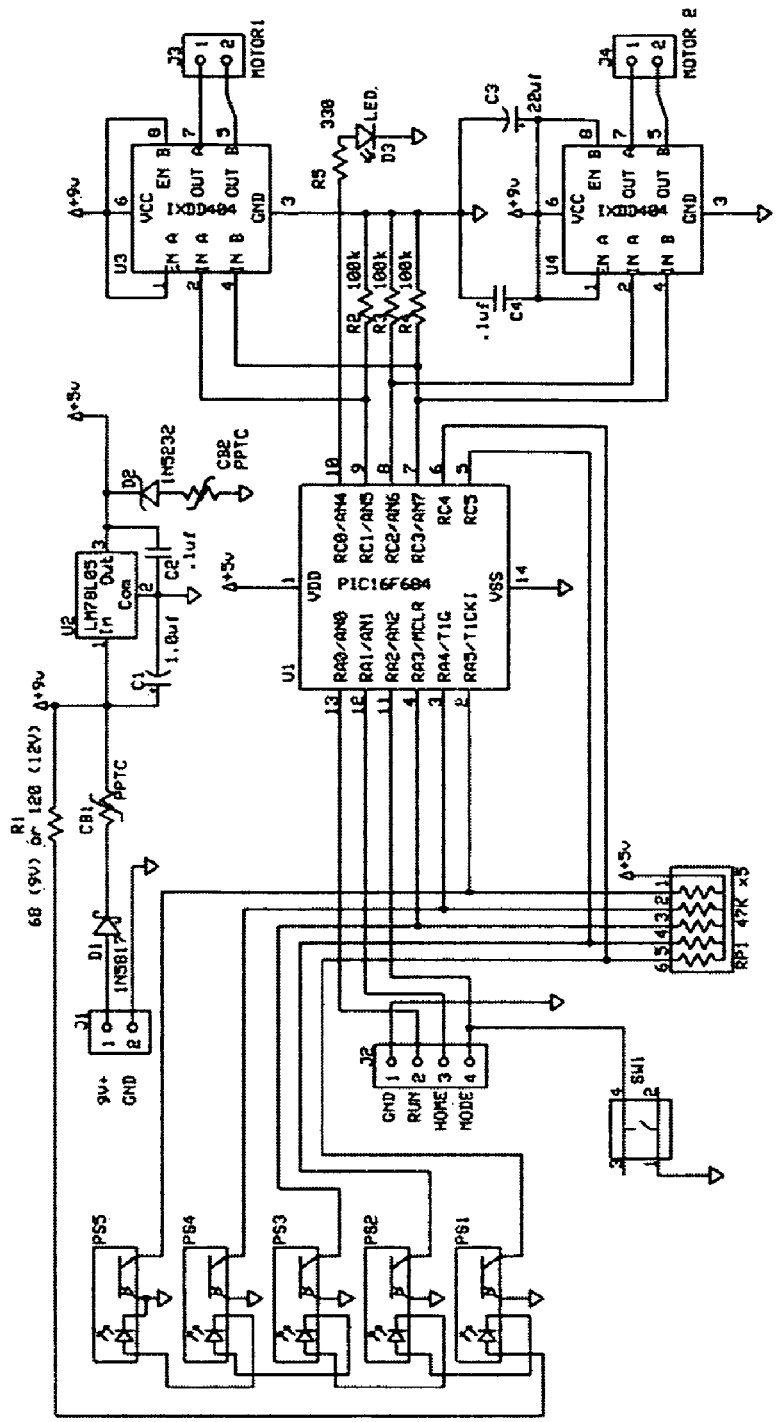
FIG. 5 is a representative schematic of showing the sensor positions for the biopsy device accordance with an embodiment of the present invention.

The assembled mechanism 200 that causes the translations and movements of the parts of the syringe/biopsy assembly 645 is illustrated in FIG. 2 positioned within the device 100. The components of the mechanism 200 are illustrated individually, and in more detail, in FIGS. 6-12. As stated heretofore, the movement of the mechanism 200 is controlled by the electronic components positioned on the circuit board 300 with surfaces bottom 305 and top 350, the positioning of which can be seen in this Figure. The surfaces of circuit board 300 are illustrated in more detail in FIGS. 3 and 4. The actual physical layout of the circuit board 300 is not critical, with the exception of the sensor placement, and will be known to this skilled in the art. An example of a circuit schematic is illustrated in FIG. 5 although alternate schematics will be evident to those skilled in the art. The sequence of steps in performing the procedure is presented in FIGS. 11 through 18.

Figure 3:
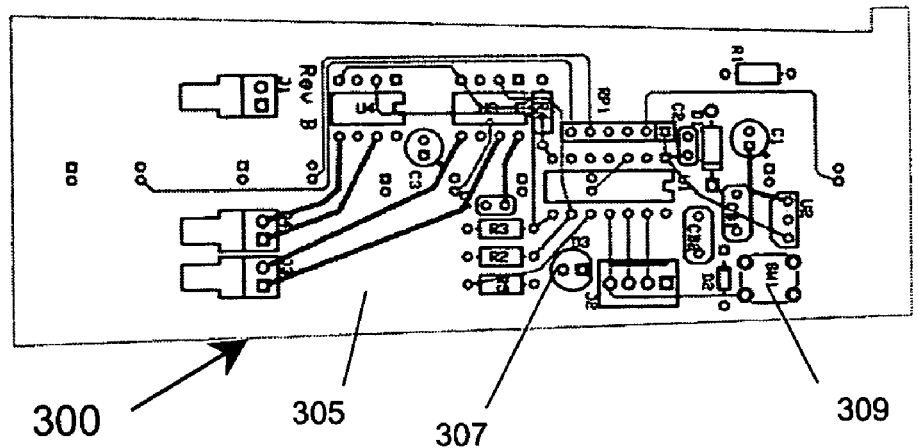
FIG. 3 is a bottom view of a circuit board for use in the device of FIG. 1 accordance with an embodiment of the present invention.

An electrical circuit and software control the mechanism 200 along with position (proximity) sensors 355, 356, 357, 358, and 359 that are located on the top surface 350 of the circuit board 300 The function of each sensor is described in more detail with respect to FIGS. 13-18. FIG. 3 shows the lower surface 305 of an example circuit board on to which the electrical components required to control the motors are mounted. Situated on the lower surface 305 is an LED 307 to provide power status and motor control indication. The motor control can be automatic or the motors can be controlled individually by means of a contact switch 309 on the circuit board 300. FIG. 4 shows the top surface 350 of circuit board 300 and the position sensors, 355, 356, 357, 358, and 359 that are photosensitive, infrared sensors or similar proximity sensors that detect the presence of the physical components of the mechanism 200. These sensors 355, 356, 357, 358, and 359 are mounted on the top surface 350 of circuit board 300 at the appropriate positions below the corresponding moving parts of the mechanism 200.

Figure 6:
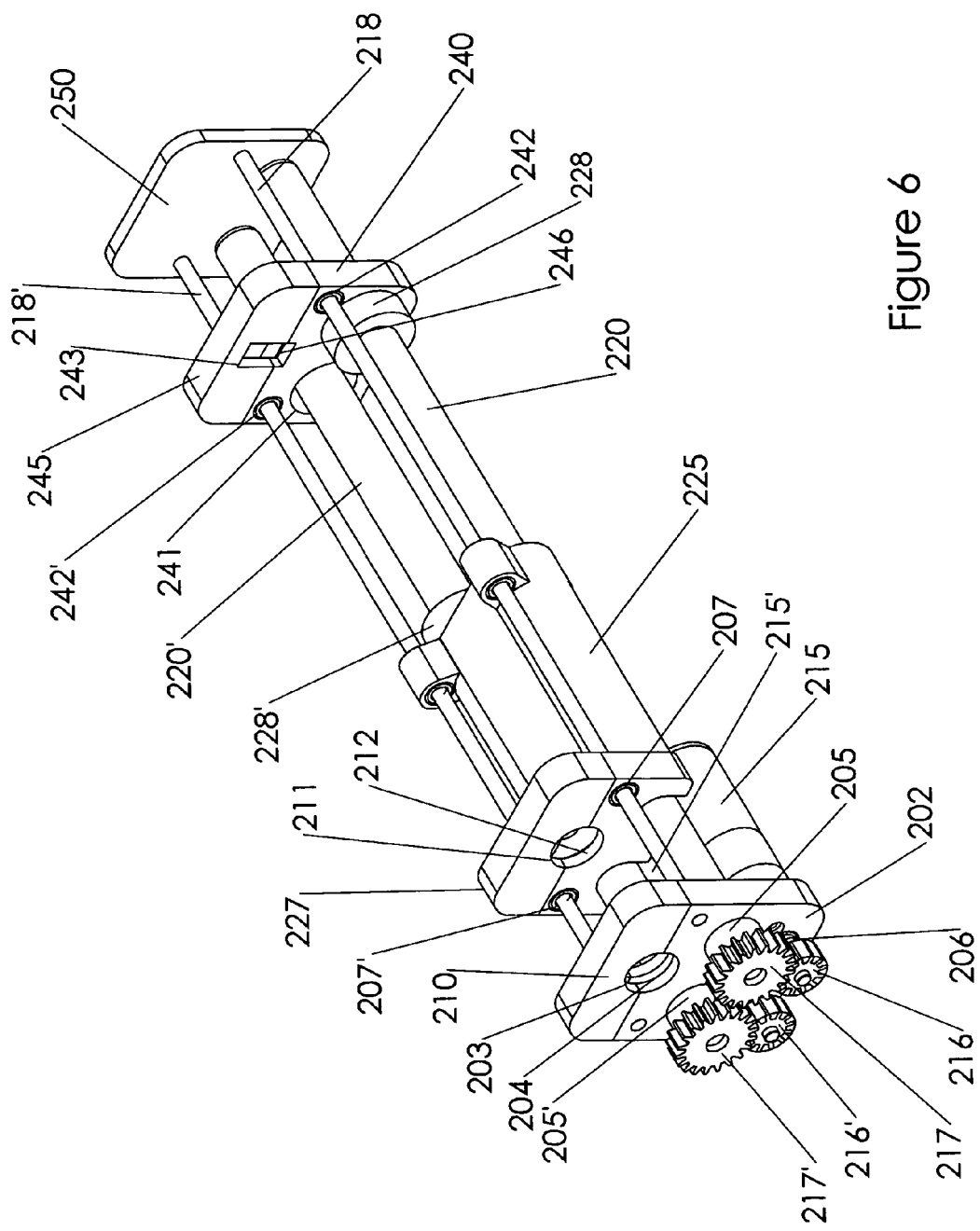
FIG. 6 is a perspective view of the interior mechanical mechanism of the biopsy device in accordance with an embodiment of the present invention.
Figure 7:
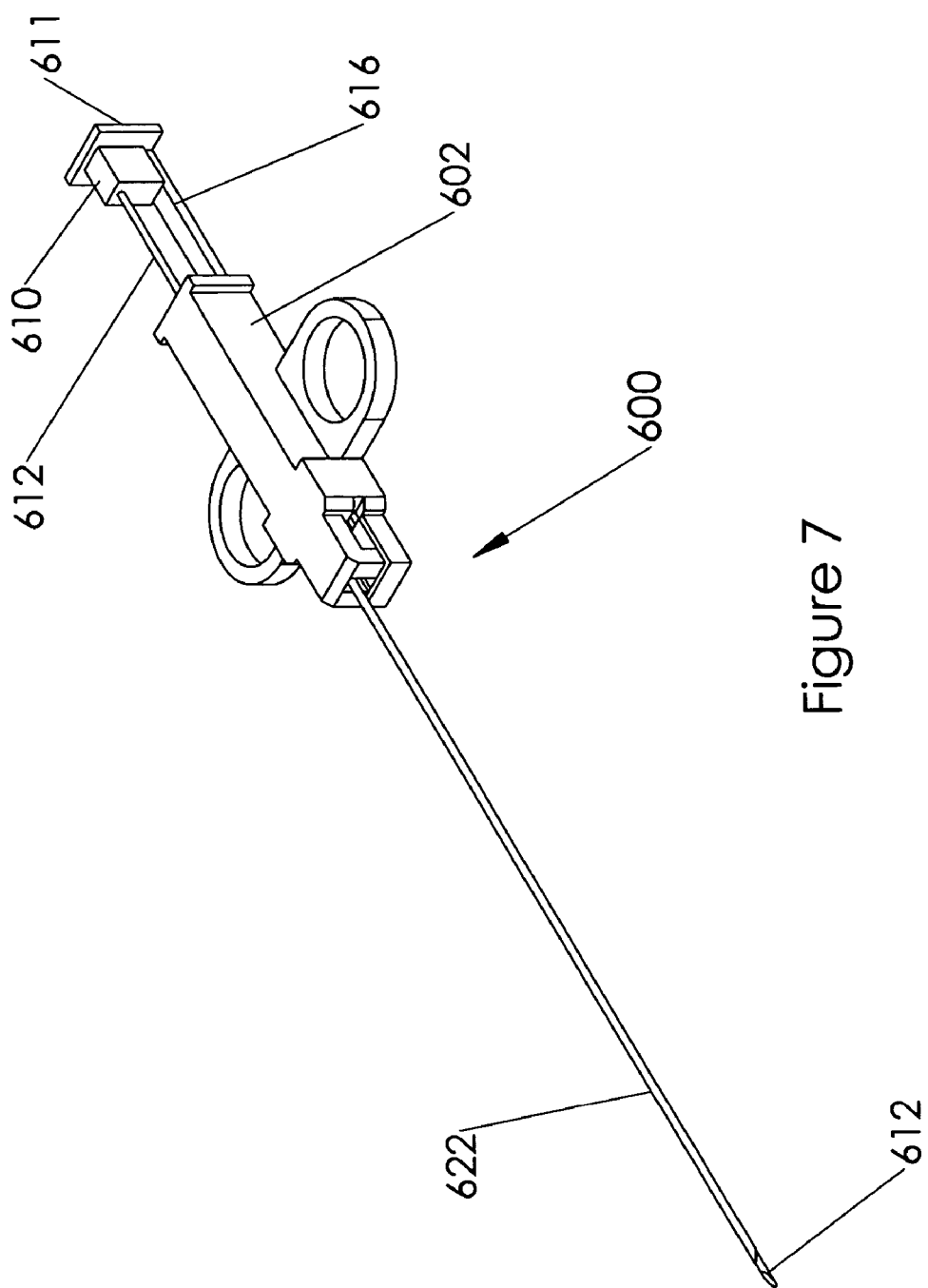
FIG. 7 is a perspective view of the trigger and cannula of the biopsy device in accordance with an embodiment of the present invention.
Figure 8:
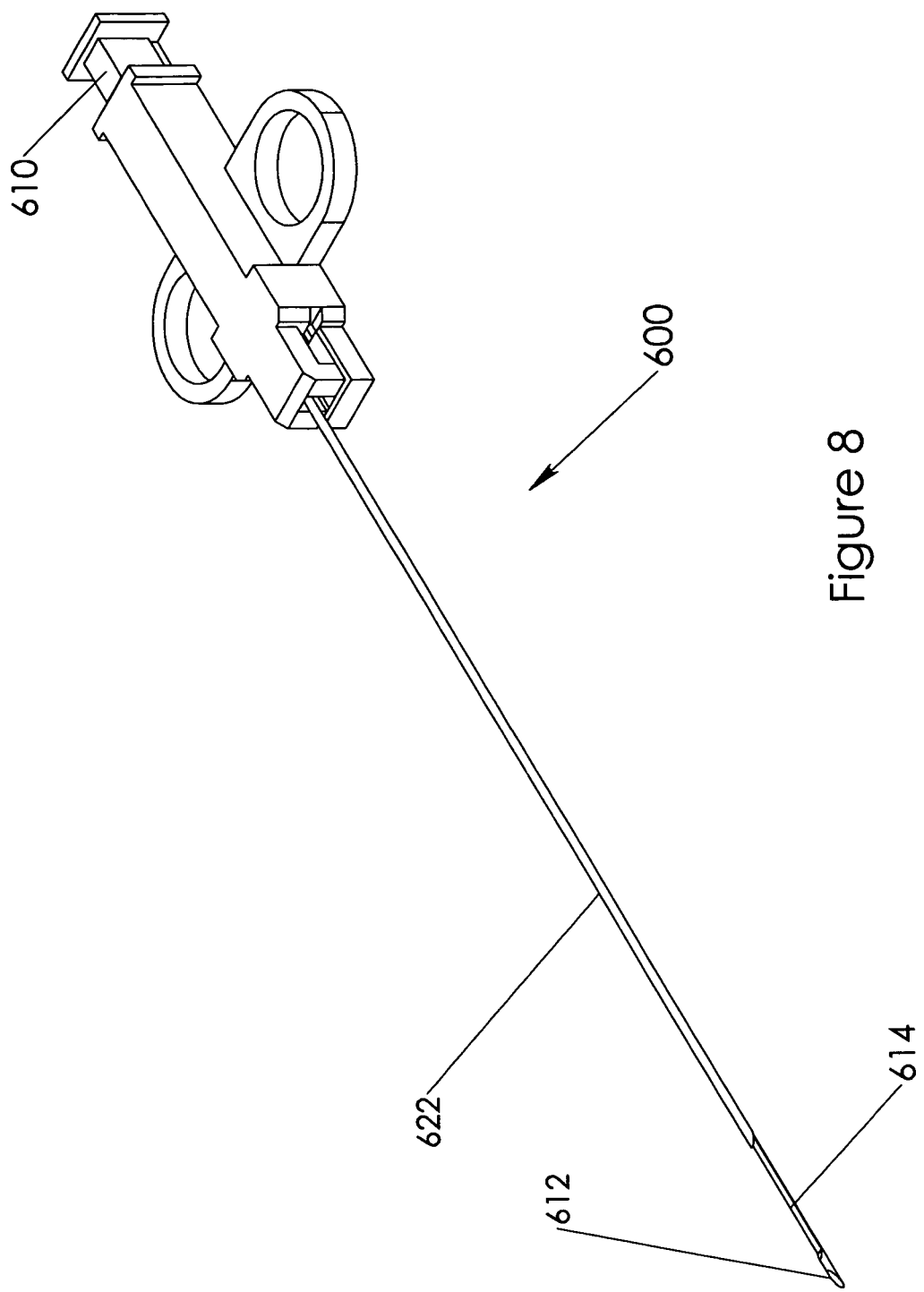
FIG. 8 is a perspective view of the trigger and cannula of FIG. 7 with the trough extended in accordance with an embodiment of the present invention.

FIG. 6 shows the mechanism 200 that is responsible for driving the biopsy needle/coagulant assembly 645 in the proper sequence. Motor A 215 is used to move the biopsy trigger block 240. Motor A 215 is attached to the front plate 202 with its shaft passing through the front plate 202 and bushing 206, to rotate gear 216 which in turn rotates the gear 217 attached to lead screw 220 and supported in plate 202 by bushing 205. The lead screw 220 extends the length of the mechanism 200 from the front plate 202 to the back plate 250. Rotation of the lead screw 220 through Acme nut 228 causes the biopsy trigger block 240 to translate on the guide rods 218 and 218' by means of the bushings 242 and 242'. The biopsy trigger block 240 has a removable top plate 245 that is connected to the trigger block 240 by any means known to the art, such as hinge, slip or snap fit, etc. To insert the biopsy trigger flange 611 (FIG. 7) within the slot 246 in opening 243, the top plate 245 is removed at the time of insertion of the syringe/biopsy assembly 645 to enable the biopsy trigger flange 611 to fit within the opening 243. Likewise top plates 227 and 210 are removed to allow placement of the plunger flange 664 and syringe flange 654 of the assembly 645 in respective slots 221 and 204 within block 205 and plate 202, respectively. Once inserted, the respective top plates are replaced on the top of the respective blocks, thus holding the assembly 645 in place. Using a precision, Acme threaded rod (such as McMaster Carr, Part Number: 98940A1, ⅜", right hand, 5 start) for the lead screw 220 provides sufficient translation per revolution of the biopsy trigger block 240.

Motor 215' moves the syringe plunger block 225 to inject the coagulant material from the syringe. The syringe plunger block 225 is a L-shaped unit with the leg of the L being created by the syringe plunger top plate 227. Motor 215' is attached to front plate 202 and, as described above with respect to motor 215, the shaft passes through a bushing (not shown), to rotate gear 216' which in turn rotates the gear 217' and subsequently the lead screw 220' supported in the front plate 202 by bushing 205'. The lead screw 220' extends the length of the mechanism 200, ending at back plate 250 after passing freely through hole 241 in block 240. Rotation of the lead screw 220' through Acme nut 228' causes syringe plunger block 225 to translate on the guide rods 218 and 218' by means of the bushings 207 and 207'. Syringe plunger block 225 has a top 227 that is removable to enable the plunger flange 664 to be placed within the slot 212 in opening 211. Once in place, the top 227 fits on top of the block 225 and holds the plunger flange 664 in place. As with the blocks 225 and 240, the top 210 of the front block 202 is removable. The syringe flange 654 fits within the slot 204 in opening 203. The top 210 fits on top of the block 202 to hold the flange 654 in place.

For either motor, clockwise rotation of the motor causes backward movement of the respective block and vice versa.

Figure 9:
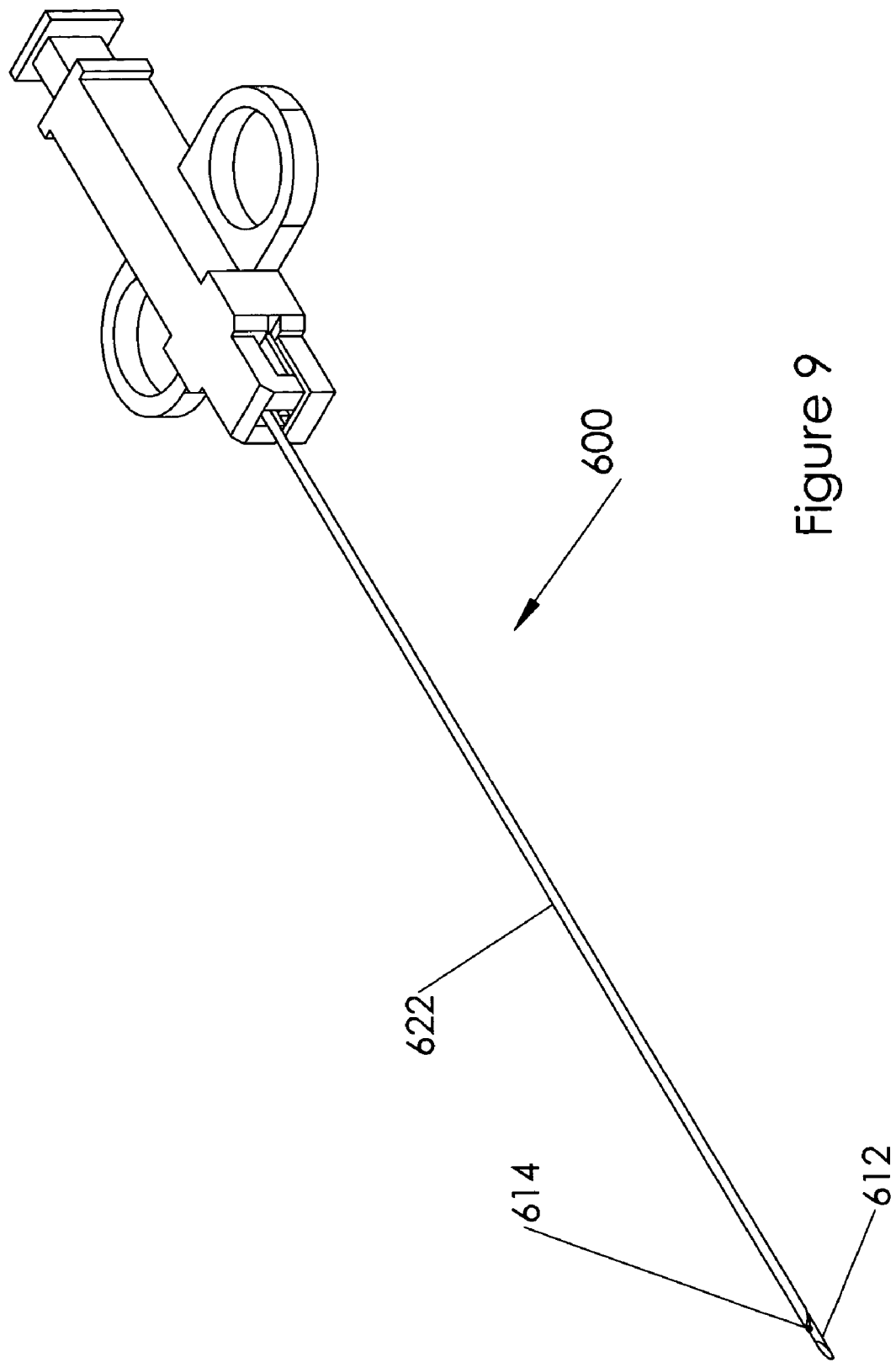
FIG. 9 is a perspective view of the trigger and cannula of FIGS. 7 and 8 after entrapping a sample in accordance with an embodiment of the present invention.
Figure 10:
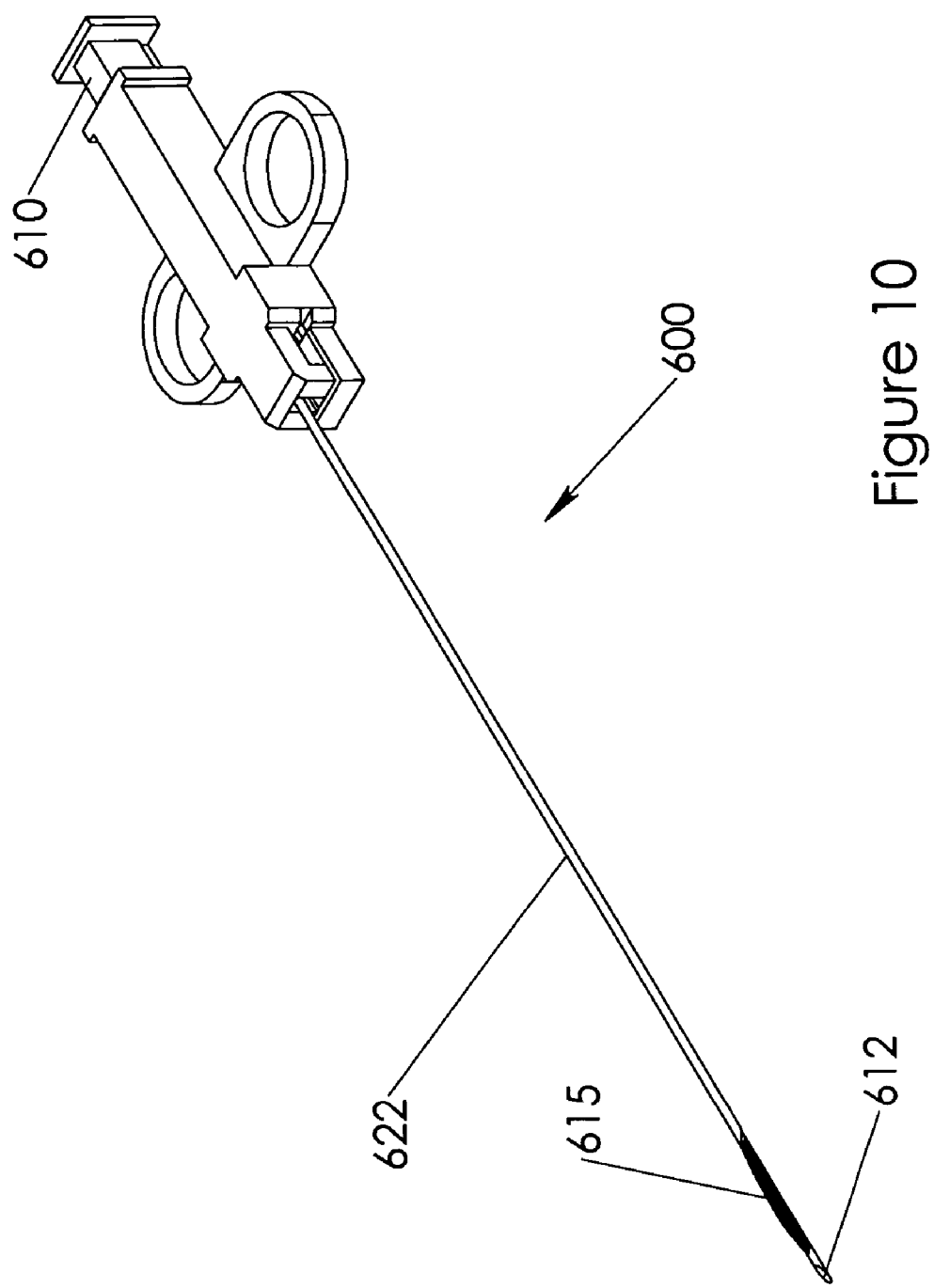
FIG. 10 is a perspective view of the trigger and cannula in a position to retrieve the specimen from the biopsy device in accordance with an embodiment of the present invention.

The device uses a standard, commercially available, spring action, semi-automatic biopsy device 600, well known by those in the art, and other types of biopsy devices can be substituted with slight modifications to the mechanism 200. The examples of biopsy devices provided in Table 1, and shown in FIGS. 7 and 8 can be used with disclosed mechanical mechanism 200 without modification. The biopsy device 600 has a trigger 610, to which is attached a stylet 612 having a specimen trough 614 at the distal end. The stylet 612 is enclosed within a cannula 622 which is affixed to the internal slide within body 602. A catch arm 616 extends from the trigger 610 into the body 602 of the device 600. As the trigger 610 is pulled back, the end of the catch arm 616 engages the internal slide to which the cannula 622 is attached and allows stylet 612 to pass free through it. The enclosed internal slide is held in place, against an internal spring within body 602 by a catch mechanism. When the trigger 610 is pushed forward, FIG. 8, the trough 614 is exposed to the tissue which prolapses into the trough 614. Pushed all the way in, the catch arm 616 releases the internal slide from the body 602 which, due to the stored energy of the spring, is propelled forward and the attached cannula 622 entraps a sample of tissue within the trough 614 of stylet 612 (FIG. 9). Once the specimen is obtained, the biopsy device 600 is removed. The trigger 610 is pulled back to retract the cannula and then advanced without releasing the internal slide and the tissue sample 615 retrieved.

The disclosed invention automates this operation sequence. While designed for the semi-automatic device, other means of automating the action of the individual stylet (needle) and cannula combination or the other biopsy obtaining devices could be accomplished by those skilled in the art and incorporated in to the invention.

While designed for the use of a semi-automatic cutting needle biopsy device, other biopsy devices such as an aspiration needle or suction needle can be adapted for use with the automated device.

While designed using a mechanical mechanism for translation and movement of the biopsy device and syringe, suitable pneumatic, hydraulic and/or electromechanical mechanisms could be employed by those skilled in the art and incorporated into the invention to achieve the same effect of taking a biopsy and delivering a coagulant or other material.

Figure 11:
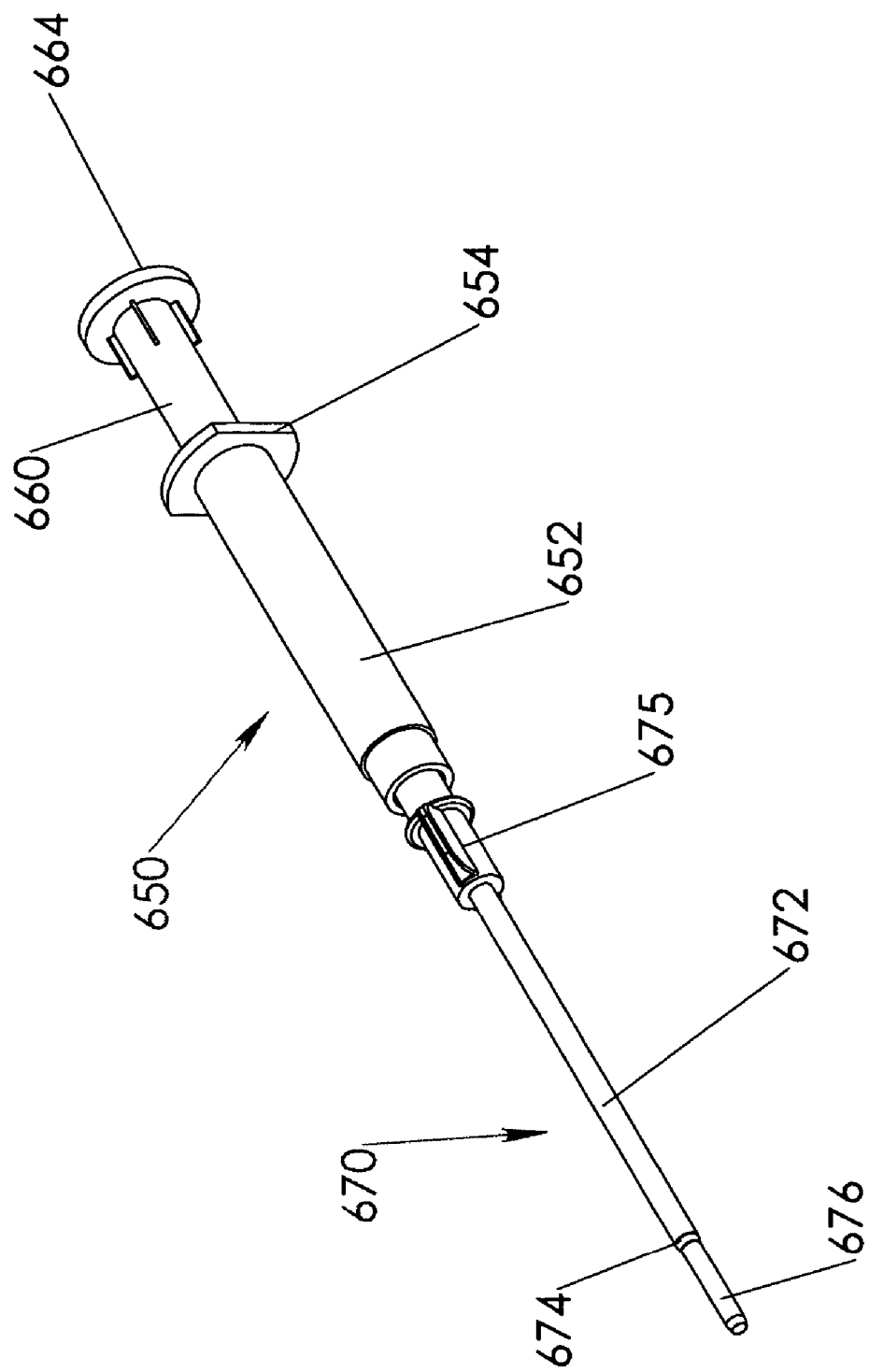
FIG. 11 is a perspective view of the biopsy syringe in accordance with an embodiment of the present invention
Figure 12:
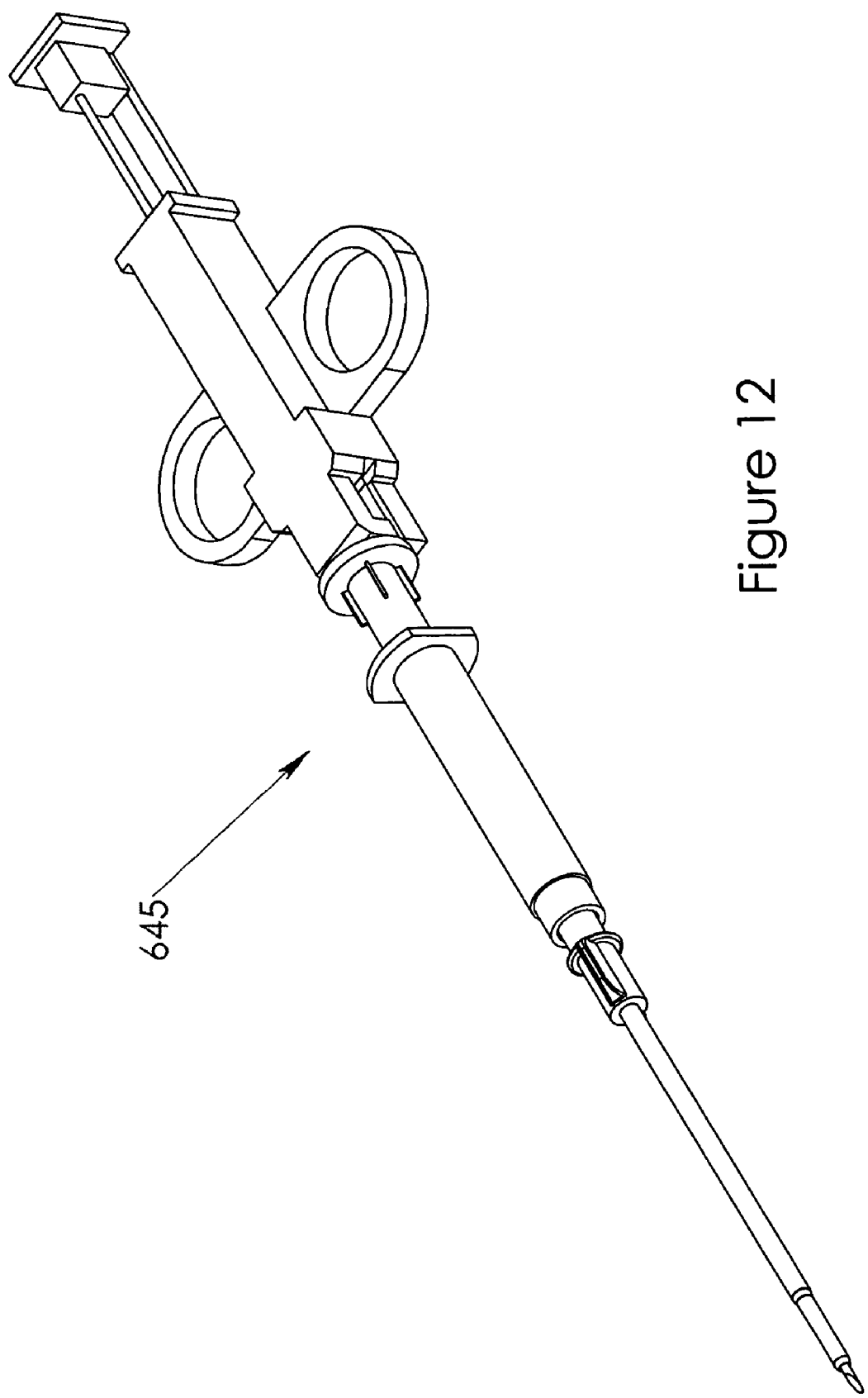
FIG. 12 is a perspective view of the syringe of FIG. 11 mounted on the trigger in accordance with an embodiment of the present invention.

The functional and operative position of the cutting/syringe apparatus 645 is shown in FIGS. 11 through 18 for a biopsy with a coagulant application material. The biopsy syringe 650 is composed of a syringe barrel 652 with a flange 654, a delivery sheath assembly 670, having a distal section 676, and a plunger 660 with a flange 664, as illustrated in FIG. 11. As indicated in this Figure, and will be described in detail hereinafter, the delivery sheath 670 has a connector 675 for attachment to the syringe 650, a proximal portion 672 and a transition section 674. A user-defined volume of coagulant is drawn up into the fluid chamber of the syringe barrel 652 using customary techniques. As illustrated in FIG. 12, the style 614 and cannula 622 of the semi-automatic biopsy device 600 are passed through the biopsy syringe 650 and application sheath 670 according to the teachings of Krause, co-pending U.S. patent application Ser. No. 10/858,112 ("Biopsy and Delivery Device", field Jun. 1, 2004).

Figure 13:
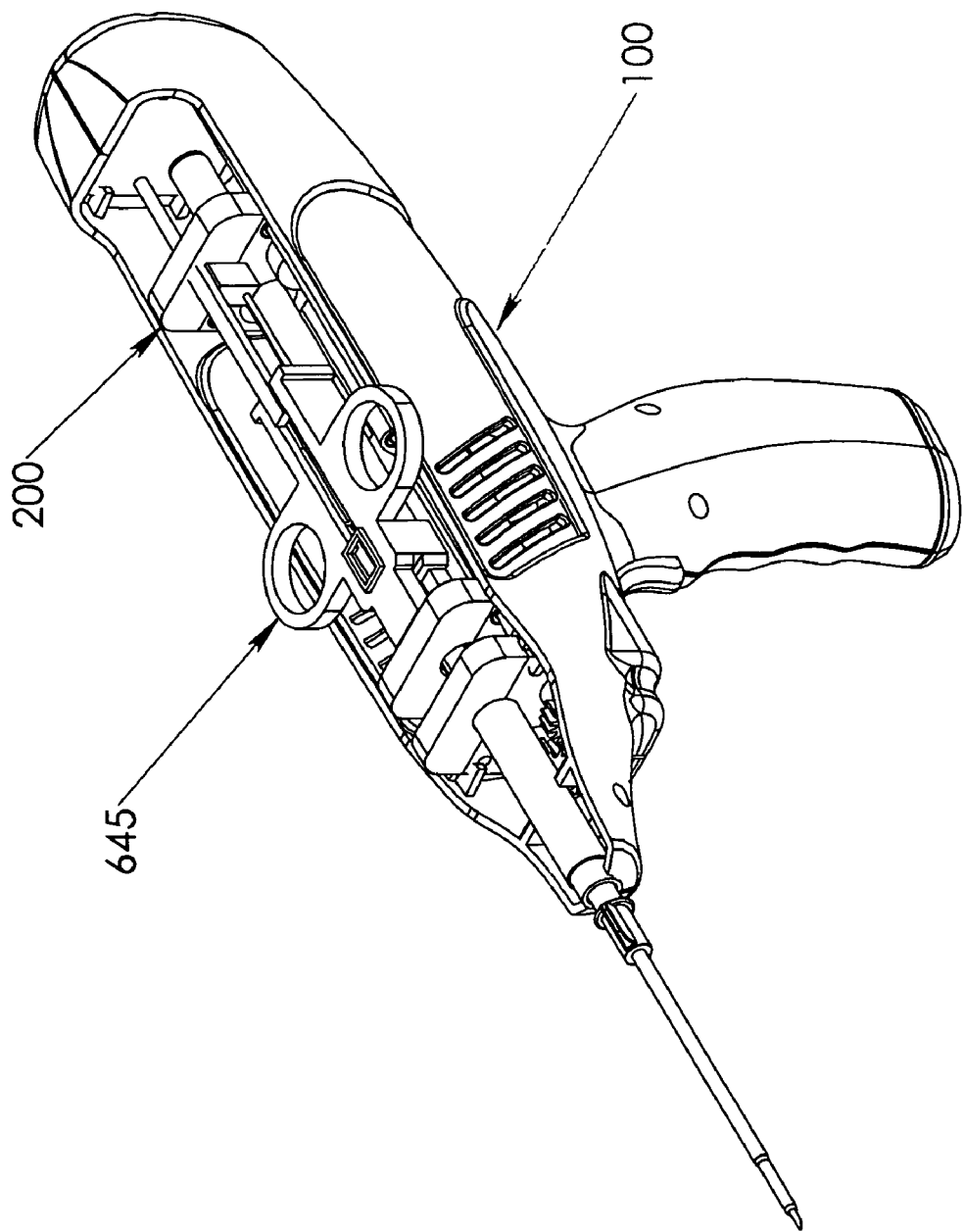
FIG. 13 is a cutaway top perspective view of the syringe and trigger combination of FIG. 12 mounted on the automatic biopsy device in accordance with an embodiment of the present invention.
Figure 14:
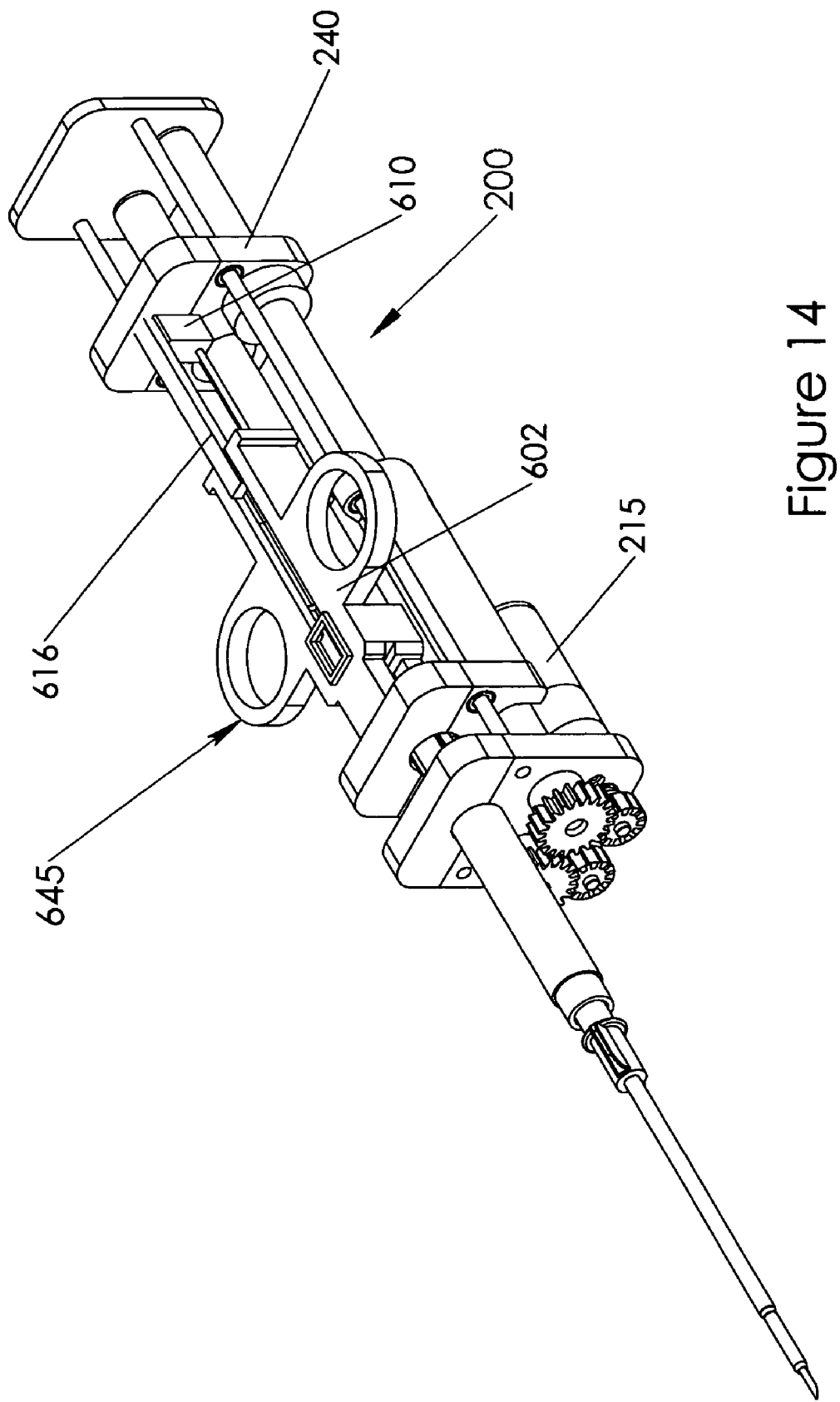
FIG. 14 is a view of the mechanism of FIG. 6 in the "Home" position in accordance with an embodiment of the present invention.
Figure 15:
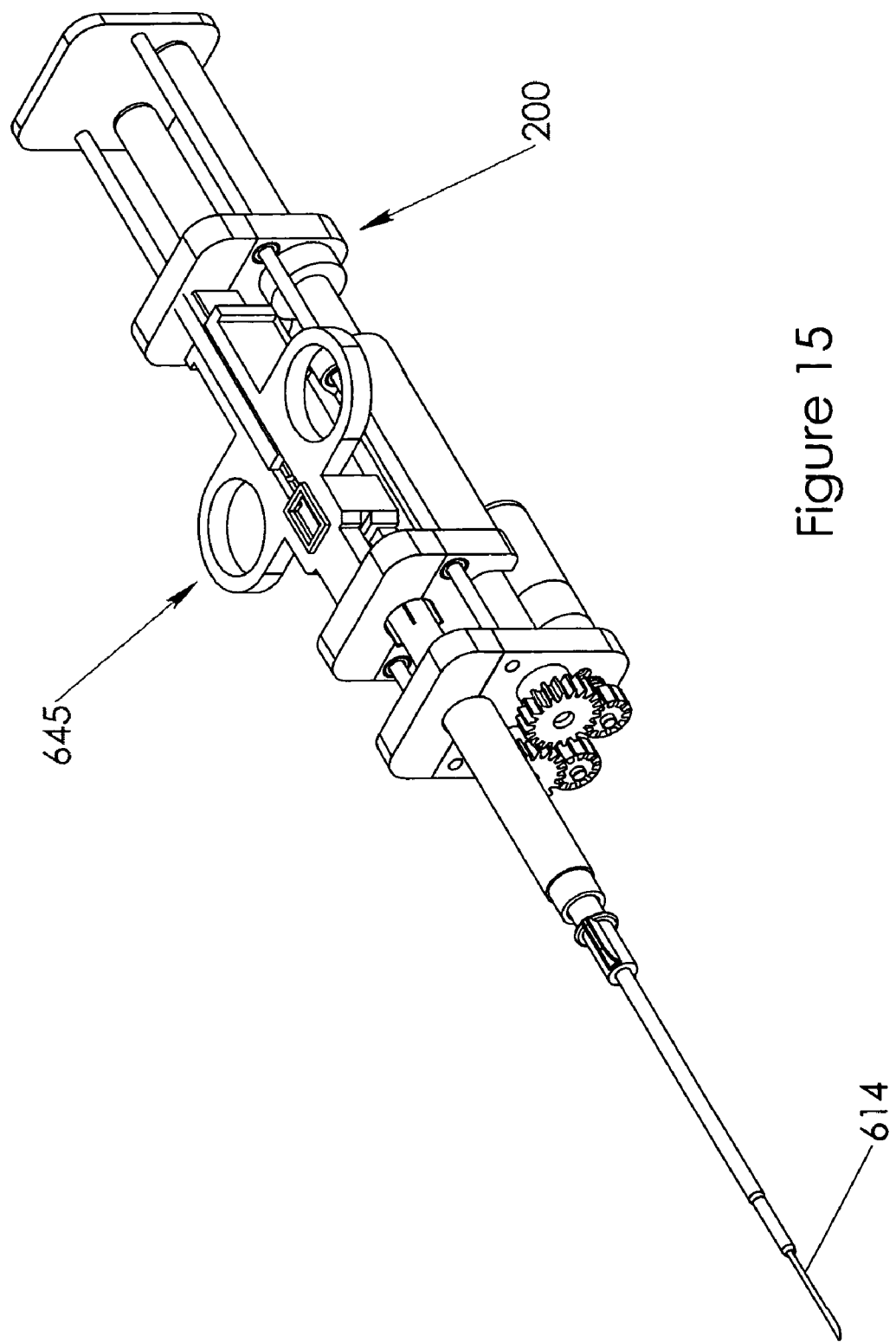
FIG. 15 is a perspective view of the biopsy device illustrated in FIG. 14 in the "Run" position with the cannula and stylet in a position to extended into the tissue in accordance with an embodiment of the present invention.
Figure 16:
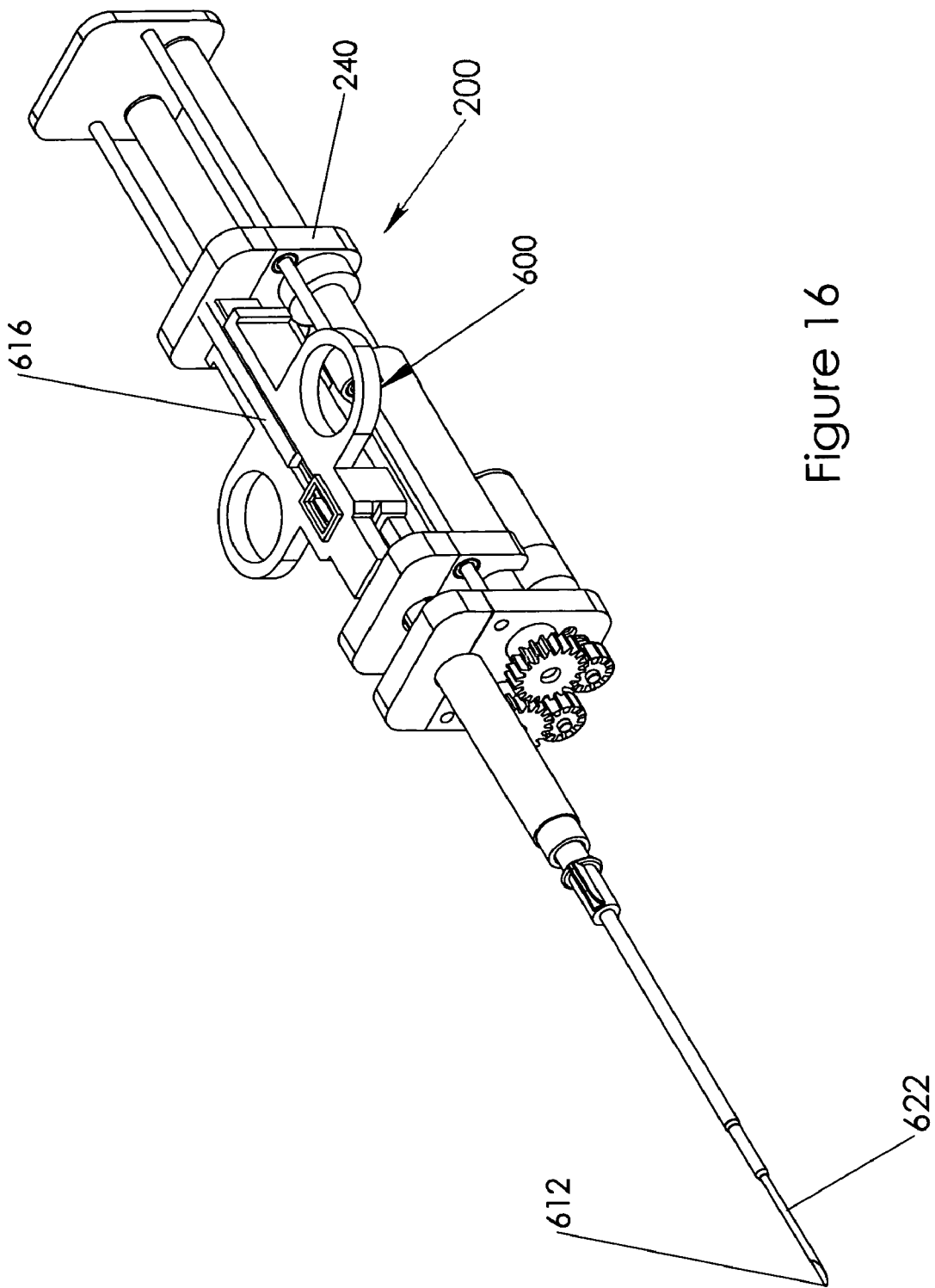
FIG. 16 is a perspective view of the biopsy device with the cannula being extended to cover the stylet entrapping the specimen in accordance with an embodiment of the present invention.
Figure 17:
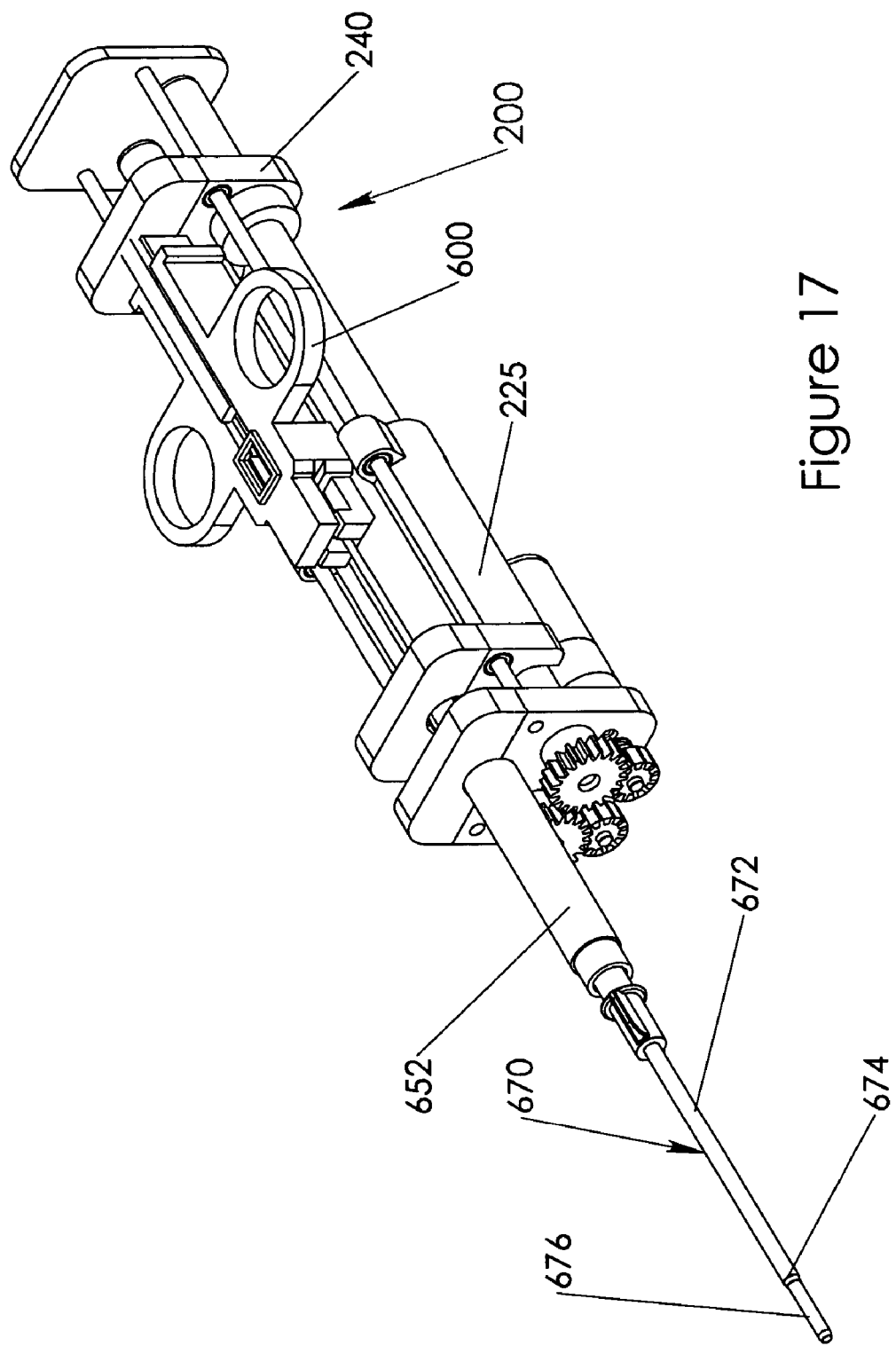
FIG. 17 is a perspective view of the biopsy device with the cannula being retracted in accordance with an embodiment of the present invention.
Figure 18:
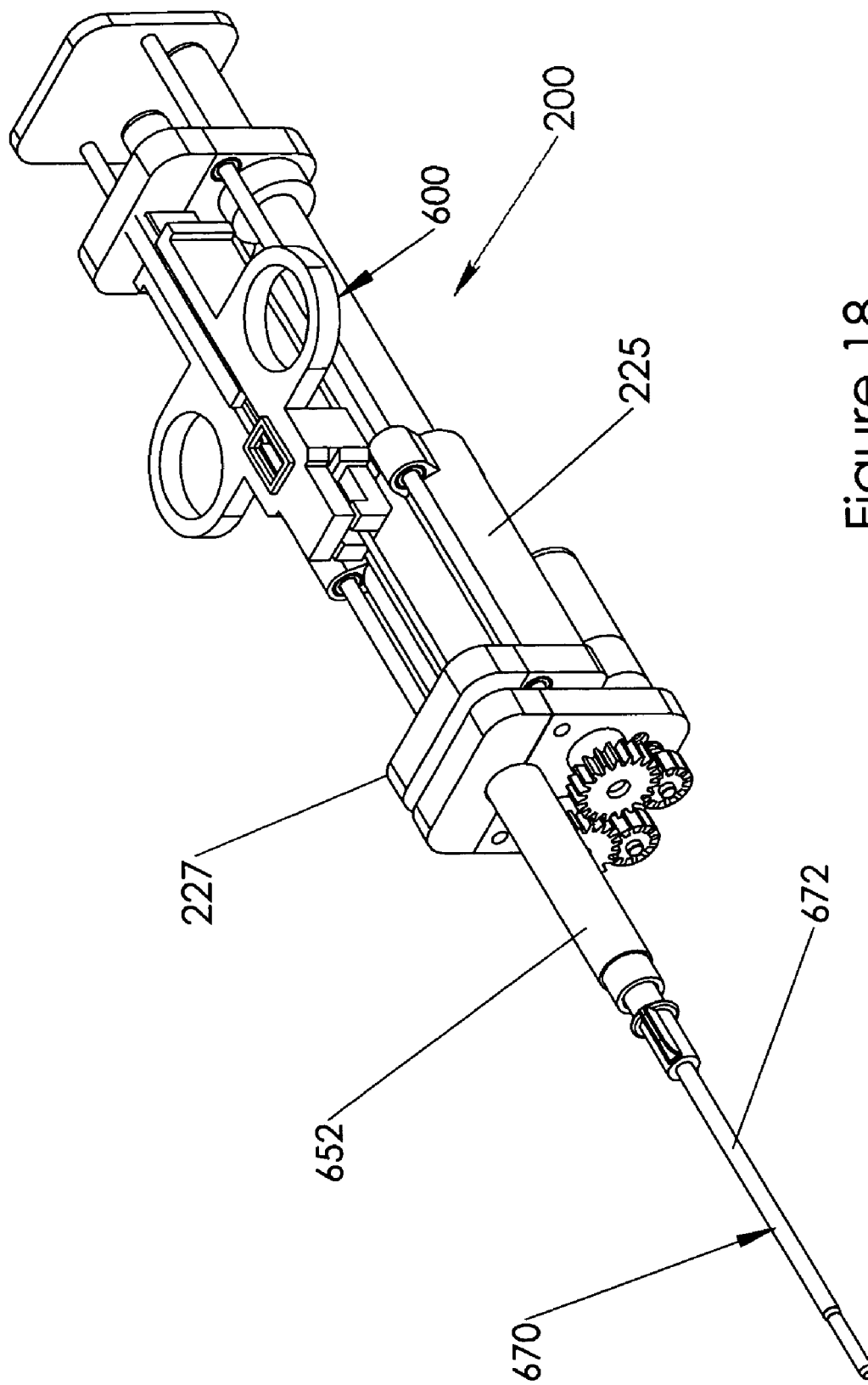
FIG. 18 is a perspective view of the biopsy device at the point of completion of the process in accordance with an embodiment of the present invention.

The complete, syringe and biopsy assembly 645 of FIG. 14, is inserted into the mechanism at the Home position, after the top 120 of the biopsy device 100 has been opened. As illustrated in FIG. 13, the syringe barrel flange 654 is inserted into the slot 204, the syringe plunger flange 664 into the slot 212 of block 225 and the biopsy trigger flange 611 into slot 243 of block 240 as described in FIG. 6. The tops for the respective blocks are replaced to hold the respective flanges in place.

The biopsy needle software is controlled using the trigger mechanism 125 that activates the power applied to the unit from the battery pack 135. Whenever power is applied to the unit the trigger 125 is active and has two positions: Home and Run. A button 309 located on the circuit board 300, enables the user to manually adjust the position of each block by causing each motor to move forward or backwards. Each motor is moved individually, one at a time. There is also an LED 307 for indication of status, such as: Run, Home, battery low, automatic or manual.

Referring to FIG. 6, when activated by the trigger 125 and control circuit 300, the motor A 215 rotates the lead screw 220, thereby moving the biopsy trigger block 240 through the rotation of the lead screw 220. Rotating lead screw 220 through nut 228 causes block 240 to translate on the guide rods 218 and 218' by means of the bushings 242 and 242'. Using a precision, threaded rod (such as McMaster Carr, Part Number: 98940A1, 3/8", right hand, 5 start) for the lead screw 220 provides one inch translation for one revolution of the rod 220. In a similar fashion Motor B 215' refers to the motor controlling the large syringe plunger block 225 at the front of the unit which drives the coagulant out of the syringe barrel 652. Other lead screws or gears can be incorporated into the device to achieve slower or faster translation of the mechanism.

Moving the trigger 125 to the Home position causes the software to command the unit to seek the starting position for each motor. This is done by first powering motor 215' to move syringe plunger block 225 to the end of its motion at the front of the mechanism until detected by sensor 355. The sensor 355 causes the circuit to reverse the rotation of the motor 215', thus moving syringe plunger block 225 backwards seeking its home position as detected by sensor 356. The circuit then activates motor 215 to move biopsy trigger block 240 forward from its initial position looking for the starting position as referenced by sensor 358. If it detects that it is already at the starting position, or if it detects that it has run beyond the starting position, it then retracts biopsy trigger block 240 to the rear of the unit until detected by sensor 355 and then moves biopsy trigger block 240 forward until sensor 358 stops the forward motion at its Home position. Once the motors have stopped moving, the unit is ready for another command. The syringe and biopsy assembly 645 can be loaded in this Home position, FIG. 13.

Preferably the unit has thermally-triggered circuit breakers which prevent the system from damaging itself in the event that too much electrical current is drawn (i.e. if the blocks are forced into a collision for an extended period of time).

The Principle of Operation of the Mechanism

The operation of the invention with respect to the biopsy cutting needle is described in FIGS. 14 through 18, which are isolated views of the mechanism of FIG. 6.

From the Home position, as illustrated in FIG. 14, the trigger 125 is depressed to the Run position. The circuit activates motor A 215 driving the biopsy trigger 610 and attached catch arm 616 into device body 602 and the stylet 612 into the tissue, FIG. 15. The sensor 357 is positioned at the point at which the catch arm 616 releases internal slide and the cannula 622 is fired over the stylet 612 entrapping the tissue specimen, FIG. 16. The forward motion of the biopsy trigger block 240 is stopped after tripping sensor 357 and the motor B 215' is reversed pulling the entire biopsy device 600 backwards until sensor 359 detects the biopsy trigger block 240, FIG. 17. In this position the distal end of the stylet 612 and cannula 622 have been retracted into the proximal portion 672 of stylet 670 and proximal to the transition section 674 (FIG. 11) thus allowing coagulant material to flow through the distal section 676 which has an internal diameter just sufficient to allow passage of cannula 622. Motor B 215' is now activated to drive syringe plunger block 225 forward forcing the coagulant material within the syringe barrel 652 through the sheath 670, past the retracted stylet 612 and cannula 622 and into the biopsy track. Once the sensor 355 detects the presence of syringe plunger block 225, it stops the motor 215', FIG. 18, completing the procedure.

The entire device 10 is withdrawn from the patient, the top piece 120 removed and the syringe/biopsy assembly 645 is removed from the device and the biopsy sample is then retrieved from the biopsy device 600 in the customary manner.

The device can also be used to deliver a beneficial agent, such as contrast agent, thrombin, radiation treatment, or the like. The applicant material can also be used to deliver therapeutic agents, such as radioactive isotopes for localized treatment of tumors, anti-cancer agents, anti-metastatic agents, and the like. Examples of anti-cancer agents include 5-fluorouracil, cisplatin, prednisone, and others described in U.S. Pat. No. 4,619,913, which is incorporated herein by reference.

The present invention can be employed to deliver other materials other than coagulant material into a biopsy track or used to drain and fill an abscess.

While the invention has been described in detail with reference to the preferred embodiments thereof, it will be apparent to one skilled in the art that various changes and modifications can be made and equivalents employed, without departing from the present invention.

ELEMENTS LIST 100 biopsy device
115' Right outer casing
115" Left outer casing
120 removable top piece
125 trigger mechanism
130 Handle
135 battery pack
200 assembled mechanism
202 Front plate
203 Syringe opening
204 Slot for syringe flange 654
205 Bushing for lead screw 230
205' Bushing for lead screw 230'
206 Bushing for motor 215 shaft
206' Bushing for motor 215' shaft
207 Bushing for guide rod 218
207' Bushing for guide rod 218'
210 Front plate top
211 Opening for plunger 660
212 Slot for plunger flange 664
215 Motor A
215' Motor B
216 Driving gear for motor A, 215
216' Driving gear for motor B, 215'
217 Driven gear for lead screw 220
217' Driven gear for lead screw 220'
218 Guide rod 1
218' Guide rod 2
220 Lead screw for biopsy pull block 240
220' Lead screw for syringe plunger block 215
225 Syringe plunger block
227 Syringe plunger top
228 Lead screw nut for syringe plunger slide 225
240 Biopsy trigger block 241 Pass through hole for lead screw 220'
242 Bushing for guide rod 218
242' Bushing for guide rod 218'
243 Opening for biopsy pull 610
245 Biopsy trigger block top plate
246 Slot for biopsy trigger flange 611
250 Back plate
300 Circuit board
305 Lower surface of circuit board 300
307 LED indicator
309 Mode switch
350 upper surface of circuit board 300
355 position sensor
356 position sensor
357 position sensor
358 position sensor
359 position sensor
600 automatic biopsy device
602 body
610 trigger
611 biopsy trigger flange
612 stylet
614 specimen trough
616 catch arm
622 cannula
624 spring
645 syringe/biopsy assembly
650 biopsy syringe
652 syringe barrel
654 flange
660 plunger
664 plunger flange
670 delivery sheath
672 proximal portion
674 transition section
675 sheath connector
676 distal section

What is claimed is:

1. A multiple stage core biopsy assembly to automatically obtain a tissue specimen during a first stage and deliver a material in the biopsy track during a second stage, said assembly comprising:
   a. an outer casing, said outer casing having a hollow body, and a handle,
   b. a power supply, said power supply being connected to a circuit board,
   c. circuit board, said circuit board supporting electronic circuits, electrical components, and a microchip having a program, said circuit board being powered by said power supply,
   d. a single trigger mechanism, said single trigger mechanism initiating said program,
   e. a multiple stage delivery mechanism, said multiple stage delivery mechanism having motors activating and controlling movable mechanical components, said motors being activated by said program, and being supported within said body of said outer casing,
   f. a removable core biopsy unit to cut and retain tissue in said first stage, said core biopsy unit, being dimensioned to be retained and movable with said multiple stage delivery mechanism,
   g. a removable material delivery unit, adjacent to and actuating independent of said core biopsy unit, to deliver said material into said biopsy track in said second stage, said removable material delivery unit being dimensioned to be retained within and positioned to be moved by said multiple stage delivery mechanism,
   wherein said mechanical components within said multiple stage delivery mechanism move said core biopsy unit during said first stage to take said biopsy and said material delivery unit to deliver said material to said biopsy track during said second stage, said core biopsy unit and said material delivery unit forming a biopsy/delivery sub-assembly.

2. The assembly of claim 1 wherein said power supply is a battery pack.

3. The assembly of claim 1 wherein said power supply is an external power source.

4. The assembly of claim 1 further comprising interior supports for placement and alignment of said delivery mechanism.

5. The assembly of claim 1 further comprising interior supports for placement and alignment of said circuit board.

6. The assembly of claim 1 wherein said electrical components include sensors, said sensors registering the position of said mechanical components.

7. The assembly of claim 6 wherein said sensors send a signal signifying said position of said components to said program, to trigger the next action.

8. The assembly of claim 1 wherein said delivery mechanism comprises stationary supports and movable supports, said movable supports being moved by at least one mechanical device to control the position of said biopsy/delivery sub-assembly.

9. The assembly of claim 8 wherein said stationary supports and movable supports further comprise receiving areas for placement, alignment and containment of the biopsy/delivery sub-assembly.

10. The assembly of claim 8 wherein said at least one electro-mechanical device is a pneumatic.

11. The assembly of claim 8 wherein said at least one electro-mechanical device is powered by an electric motor.

12. The assembly of claim 1 wherein:
said material delivery unit comprises:
   a syringe barrel, said syringe barrel having a needle attachment member and a delivery material retaining area,
   a needle sheath, said needle sheath attaching to said needle attachment member and being in fluid communication with said delivery material retaining area,
   a hollow plunger, said hollow plunger being dimensioned to slide within said syringe barrel and having:
      a hub at a first end, said hub having an opening dimensioned to receive a biopsy needle and a fluid seal member covering said hub,
      an open second end, said open second end being dimensioned to receive at least a portion of a biopsy unit, and
said biopsy unit comprises:
   a casing with a cannula and stylet to cut and receive a tissue specimen, said casing extending through said hub and into said needle sheath and having a diameter less than said needle sheath.

13. A multiple stage motorized biopsy assembly to automatically obtain a core biopsy tissue specimen in a first stage and deliver a material in the biopsy track in a second stage, said assembly comprising:
   a. an outer casing, said outer casing having a hollow body,
   b. a power supply, said power supply being removable batteries, said power supply being connected to a circuit board,
   c. circuit board, said circuit board supporting electronic circuits, electrical components, and a program, said electrical components including multiple sensors to monitor a delivery mechanism,
   d. a single trigger mechanism, said single trigger mechanism initiating said program,
   e. a delivery mechanism, said delivery mechanism having at least two stages of operation to separately control a core biopsy unit and a material delivery unit, said delivery mechanism being supported within said body of said outer casing and having stationary supports and movable supports, said stationary supports and said movable supports having receiving areas for placement, alignment and containment of said core biopsy unit and said material delivery unit and said movable supports being moved by motors to control the positions of said core biopsy unit and said material delivery unit, Said material delivery unit, being disposable and having:
   a syringe barrel, said syringe barrel having a needle attachment member and a delivery material retaining area,
   a circular needle sheath, said needle sheath attaching to said needle attachment member and being in fluid communication with said delivery material retaining area,
   a hollow plunger, said hollow plunger being dimensioned to slide within said syringe barrel and having:
      a hub at a first end, said hub having an opening dimensioned to allow passage of said cutting sheath and a fluid seal member covering said hub,
      an open second end, said open second end being dimensioned to receive at least a portion of a biopsy unit,
   said biopsy unit having:
      a casing to retain a needle to receive a tissue specimen and a cutting sheath, said needle being movable within said cutting sheath and having a diameter less than said cutting sheath, said needle and said cutting sheath being movable relative to each other and the said casing, said needle and cutting sheath to passed through said hollow plunger, said syringe barrel, said hub, said circular needle sheath, and to extend beyond the distal end of said needle sheath,
wherein said components within said delivery mechanism move said core biopsy unit to take a biopsy and subsequently said material delivery unit to deliver said material based upon locations sensed by said sensors and sent to said program.

14. A motorized biopsy assembly for automatically obtaining a tissue specimen and leaving a material in the biopsy track, said device comprising:
   an outer casing, said outer casing having a hollow body, said body having a removable top and a handle; a power supply, a trigger mechanism and control means,
   a delivery mechanism, said delivery mechanism having:
      a stationary front plate, said stationary front plate having a first side and a second side, a removable top plate and a syringe opening;
      a stationary back plate,
      a syringe plunger block, said syringe plunger block having a removable top and a plunger flange receiving area,
      a biopsy plunger block, said biopsy plunger block having a removable top and a biopsy trigger flange receiving slot,
      motors, said motors being affixed to said second side of said front plate,
      gearing mechanisms, said gearing mechanisms being affixed to said first side of said front plate and being in movable communication with said motors,
      guide rods, said guide rods extending from said second side of said front plate to said back plate,
      lead screws, said lead screws being connected to said motors through said gearing mechanism, a first of said lead screws controlling movement of said syringe plunger block and a second of said lead screws controlling movement of said biopsy trigger block along said guide rods,
wherein data received from said sensors moves said syringe plunger block and said biopsy trigger block to take a biopsy and deliver material to a biopsy site.

15. The motorized biopsy assembly of claim 14 wherein said syringe plunger block, said biopsy plunger block and said front plate are dimensioned to receive and control movement of a syringe/biopsy sub-assembly.

16. The method of taking a biopsy using an automated biopsy unit having an outer casing having a trigger, a power supply, multiple sensors and a movement mechanism comprising the steps of:
   a. filling a syringe barrel with a material, b. passing a stylet/cannula semi-automated unit through a plunger at one end of said syringe barrel,
c. exiting said stylet/cannula semi-automated unit through the delivery sheath of said syringe barrel to form a syringe/biopsy assembly,
d. placing said syringe/biopsy assembly into receiving areas within a front plate, a syringe plunger block and a biopsy trigger block,
e. placing said automated biopsy unit adjacent to area for biopsy,
f. activating said trigger
g. driving said stylet into tissue,
h. reading the position of said syringe plunger block by one of said sensors,
i. releasing said cannula over said stylet
j. reading the position of said biopsy trigger block by one of said sensors,
k. pulling said stylet and said cannula into said delivery sheath, activating said biopsy trigger block to push said material into the biopsy track.

* * * * *